(12) United States Patent
Thomas

(10) Patent No.: US 7,737,147 B2
(45) Date of Patent: Jun. 15, 2010

(54) METHODS AND COMPOSITIONS TO ENHANCE THE EFFICACY OF PHOSPHODIESTERASE INHIBITORS

(76) Inventor: Thomas Nadackal Thomas, 3457 Shoreline Cir., Palm Harbor, FL (US) 34684

( * ) Notice: Subject to any disclaimer, the term of this patent is extended or adjusted under 35 U.S.C. 154(b) by 1301 days.

(21) Appl. No.: 10/881,911

(22) Filed: Jun. 30, 2004

(65) Prior Publication Data

US 2005/0009835 A1    Jan. 13, 2005

Related U.S. Application Data

(63) Continuation-in-part of application No. 10/802,000, filed on Mar. 16, 2004, and a continuation-in-part of application No. 09/927,982, filed on Aug. 10, 2001, now Pat. No. 6,635,337, and a continuation-in-part of application No. 09/881,199, filed on Jul. 27, 2000, now Pat. No. 6,432,991.

(60) Provisional application No. 60/486,121, filed on Jul. 11, 2003.

(51) Int. Cl.
*A61K 31/497* (2006.01)
*A61K 31/52* (2006.01)
*A61K 31/44* (2006.01)
*A61K 31/4409* (2006.01)
*A61K 31/472* (2006.01)

(52) U.S. Cl. ............... 514/252.16; 514/262.1; 514/649; 514/283; 514/449; 514/309

(58) Field of Classification Search ............ 514/252.16, 514/262.1
See application file for complete search history.

(56) References Cited

U.S. PATENT DOCUMENTS 5,658,936 A * 8/1997 Kifor et al. .................. 514/381
6,338,862 B1    1/2002 Niazi (Continued)

OTHER PUBLICATIONS

Thomas, T. (2000) Monoamine oxidase-B inhibitors in the treatment of Alzheimer's disease. Neurobiol. Aging. 21: 343-348.

(Continued)

*Primary Examiner*—Yvonne L Eyler
*Assistant Examiner*—Donna Jagoe
(74) *Attorney, Agent, or Firm*—Robert Varkonyi; Smith & Hopen, P.A.

(57) ABSTRACT

Methods for treatment of sexual dysfunction in men and women using combinations of phosphodiesterase (PDE) type 5 inhibitors and l-deprenyl or propargylamine compounds are described. Methods of reducing the dosage and preventing the side effects of PDE type 5 inhibitors are also described. The methods comprise administering a therapeutically effective amount of l-deprenyl or propargylamine compounds (also called monoamine oxidase [MAO] inhibitors) in combination with PDE inhibitors. Stimulation of nitric oxide production and vasodilation by l-deprenyl and propargylamine compounds augments the actions of PDE inhibitors or other drugs and methods used in the treatment of sexual dysfunction. The composition described here enhances the actions of PDE inhibitors primarily by increasing the generation of cyclic GMP by stimulating the nitric oxide pathway and secondarily by providing several additional benefits such as enhanced dopamine activity. Methods of enhancing the efficacy of various PDE inhibitors in the treatment of a number of disorders other than sexual dysfunction are also disclosed.

19 Claims, 10 Drawing Sheets

Interaction of Sildenafil with L-Deprenyl in the isolated rabbit corpus cavernosa

U.S. PATENT DOCUMENTS

| | | |
|---|---|---|
| 6,395,744 B1 | 5/2002 | Adams |
| 6,403,597 B1 | 6/2002 | Wilson |
| 6,432,991 B1 | 8/2002 | Thomas |
| 6,476,037 B1 | 11/2002 | Wallace |
| 6,548,490 B1 | 4/2003 | Doherty, Jr. |
| 6,635,667 B2 | 10/2003 | Thomas |

OTHER PUBLICATIONS

Thomas, T (2001) A role for estrogen in the primary prevention of Alzheimer's disease. Climacteric. 4: 102-109.

Thomas,T, et al. (2002) Inhibition of LDL oxidation by the neuroprotective drug I-deprenyl. Neurol. Res. 24: 169-173.

Thomas, T. et al. (1998) L-deprenyl: nitric oxide production and dilation of cerebral blood vessels. NeuroReport. 9: 1-6.

Thomas, T. et al. (1998) L-deprenyl protects vascular endothelium from amyloid-beta toxicity and stimulates production of nitric oxide. In Alzheimer's disease and related disorders. (Ed. Iqbal K. et al.) pp. 493-500, John Wiley and Sons Ltd.

Maas, R. et al (2003) The pathophysiology of erectile dysfunction related to endothelial dysfunction and mediators of vascular function. Vascular Medicine 7: 213-225.

Galle G. and Trummer, H. (2003). The etiology of erectile dysfunction and mechanisms by which drugs improve erection. Drugs of Today, 39: 193-201.

Gonzalez-Cadavid, NF. and Rajfer, J. (2000) Therapeutic stimulation of penile nitric oxide synthase and related pathways. Drugs of Today. 36: 163-174.

Tomlinson J. and Wright D. (2004) Impact of erectile dysfunction and its treatment with Sildenafil: qualitative study. Brit. Med. J. 328: 1037.

\* cited by examiner

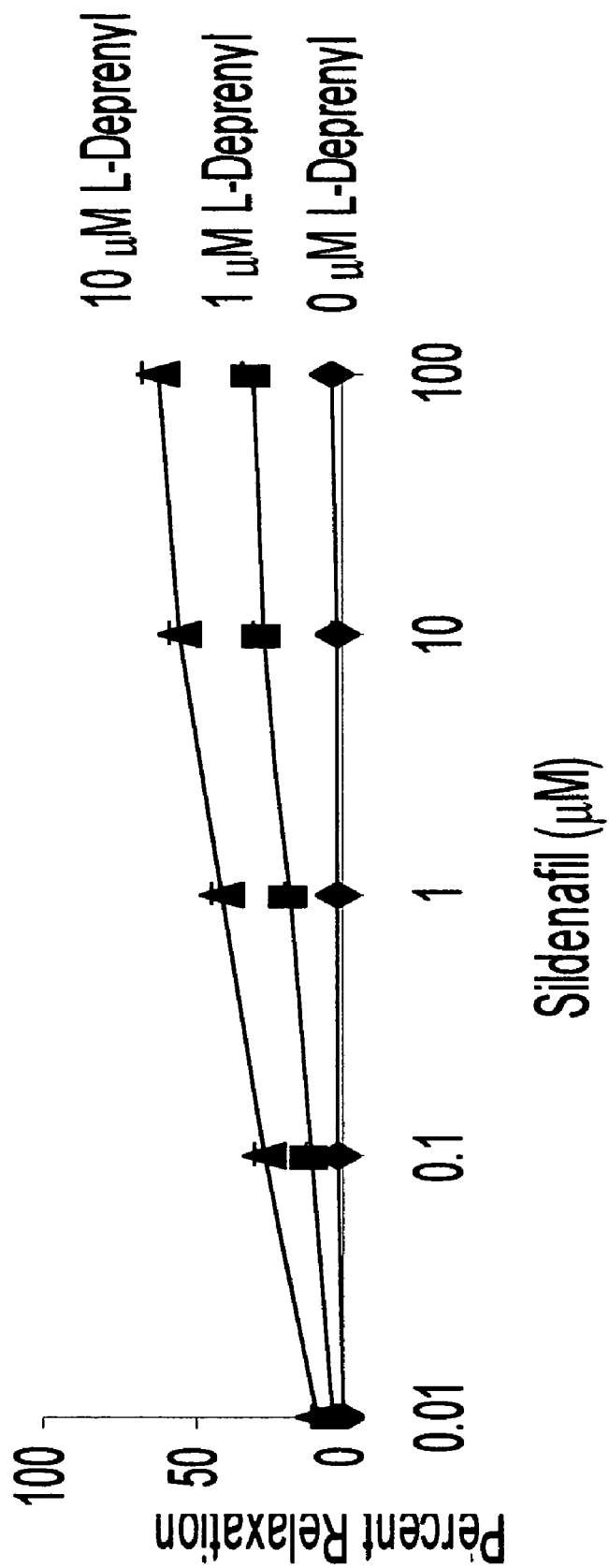
Fig. 1. Interaction of Sildenafil with L-Deprenyl in the isolated rabbit corpus cavernosa

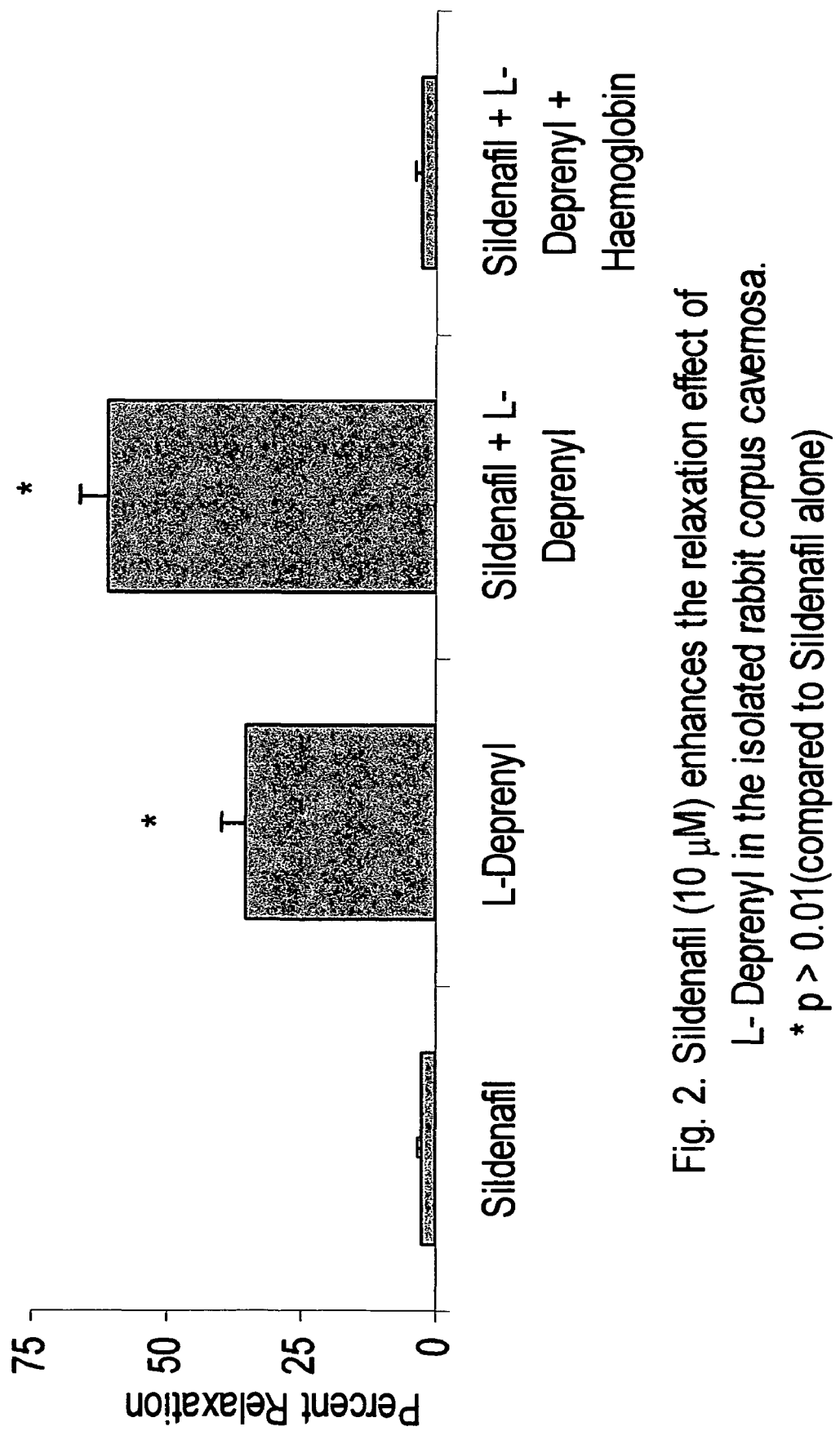
Fig. 2. Sildenafil (10 μM) enhances the relaxation effect of L-Deprenyl in the isolated rabbit corpus cavernosa.
* $p > 0.01$ (compared to Sildenafil alone)

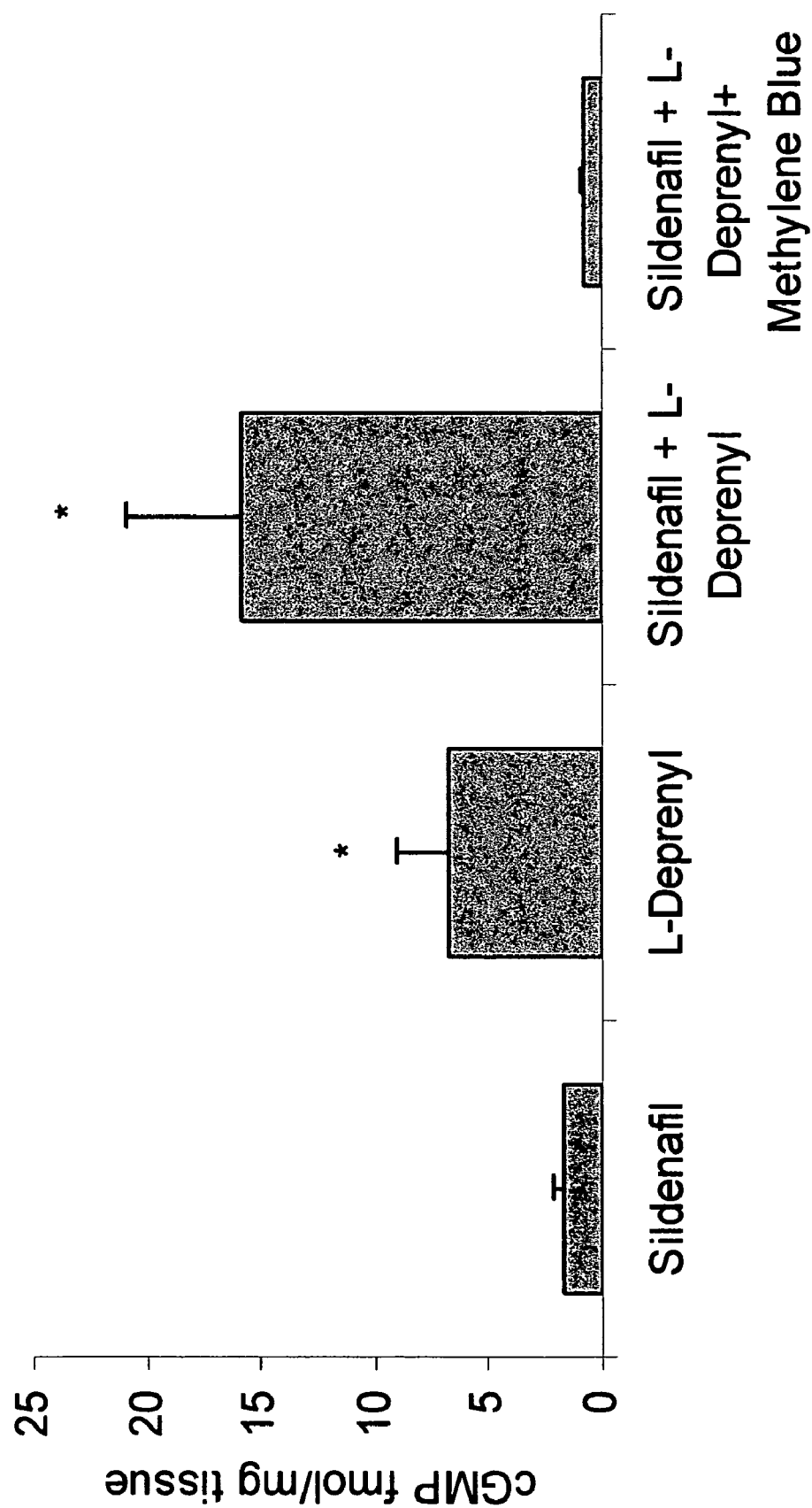
Fig. 3. Effect of Sildenafil (10 μM) and L-Deprenyl (10 μM) on cGMP formation in the rabbit corpus cavernosa.
* $p > 0.01$ when compared to Sildenafil.

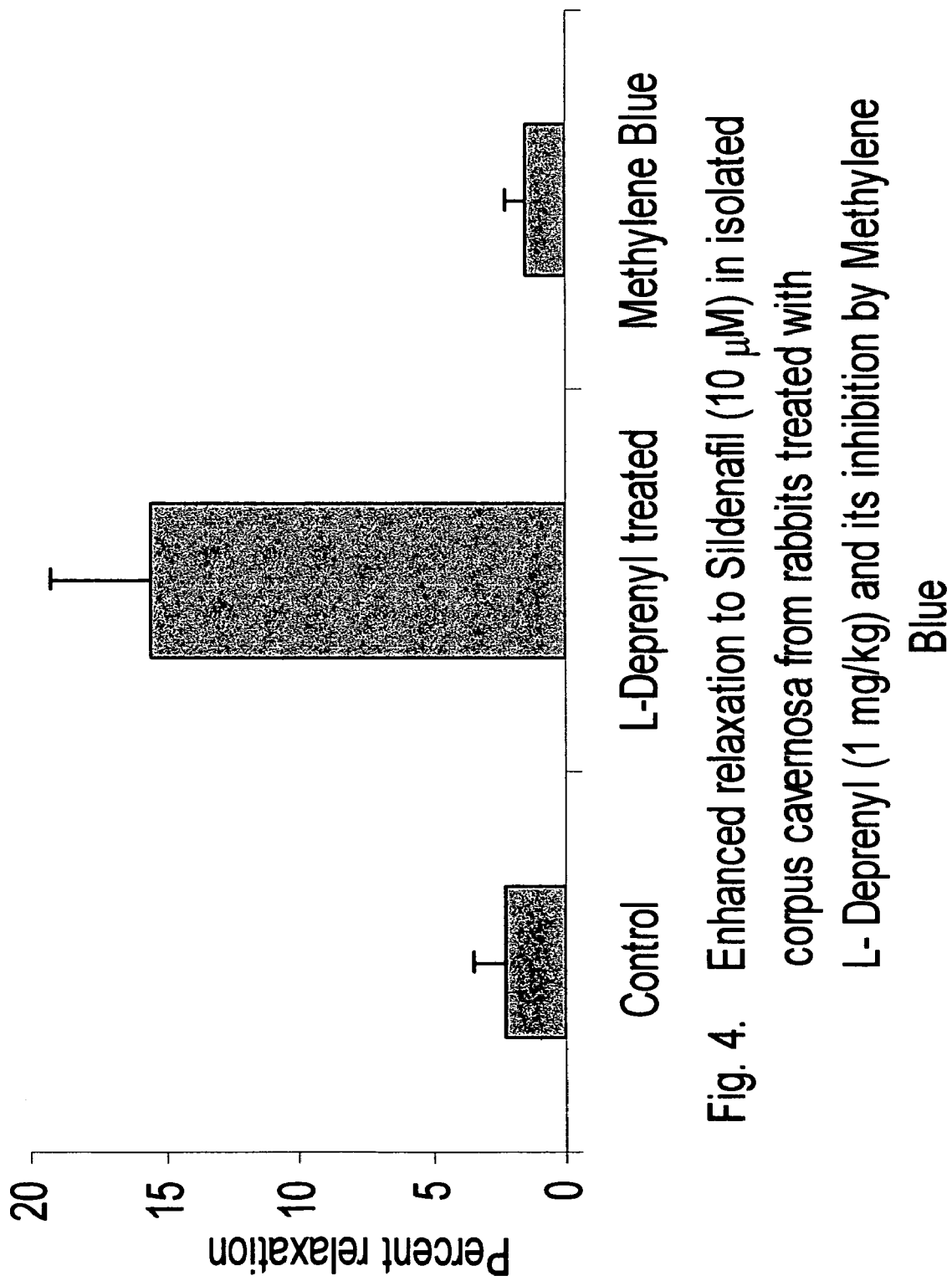
Fig. 4. Enhanced relaxation to Sildenafil (10 μM) in isolated corpus cavernosa from rabbits treated with L-Deprenyl (1 mg/kg) and its inhibition by Methylene Blue

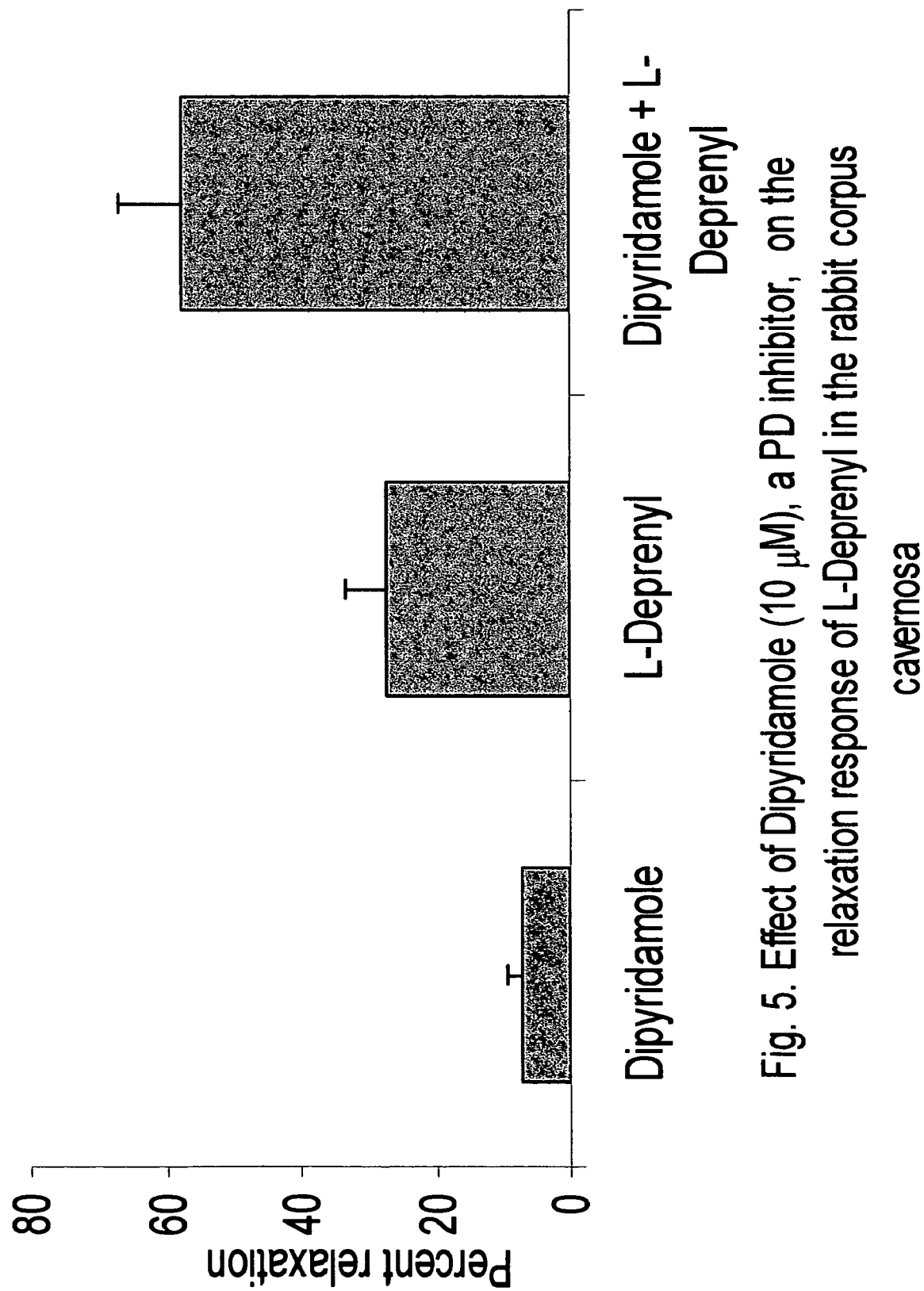
Fig. 5. Effect of Dipyridamole (10 μM), a PD inhibitor, on the relaxation response of L-Deprenyl in the rabbit corpus cavernosa

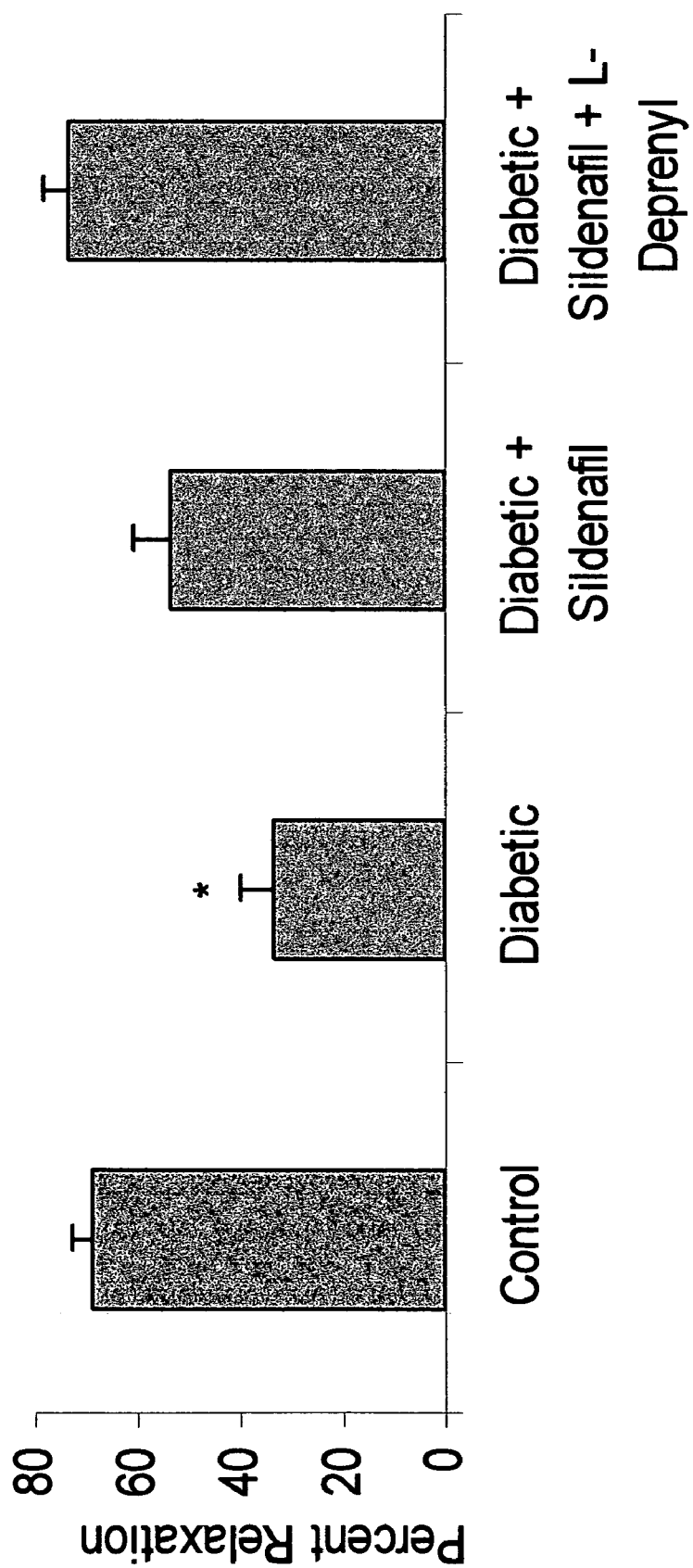
Fig. 6. Relaxation response to acetylcholine (1 μM) in presence and absence of Sildenafil (10 μM) and Sildenafil + L-Deprenyl (10 μM). * p > 0.01 when compared to control corpus cavernosa.

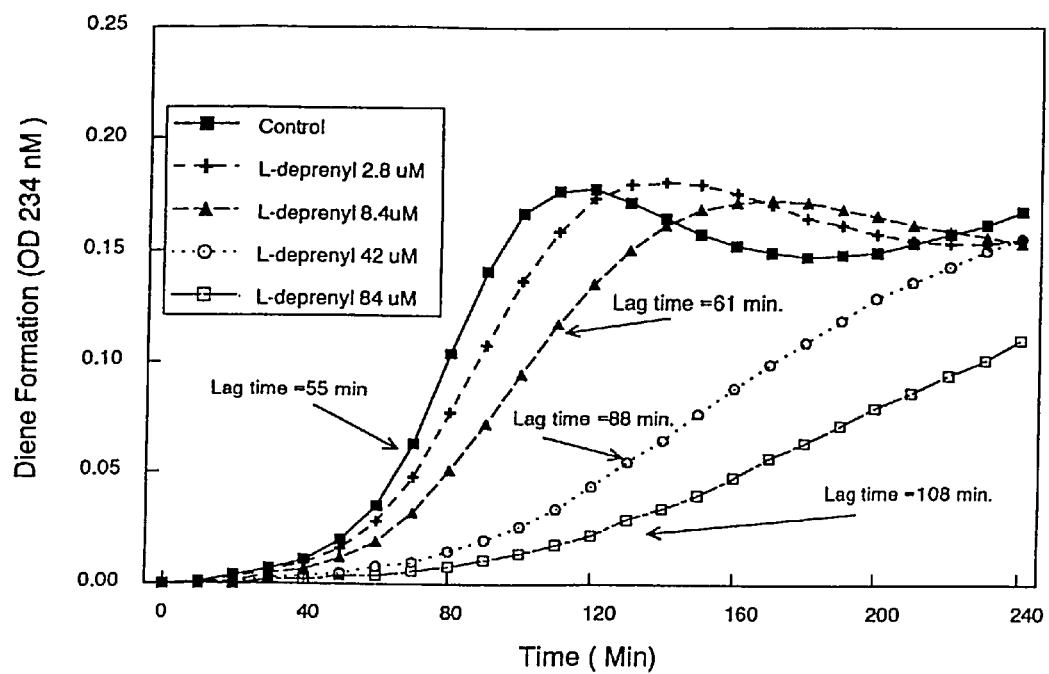
Figure 7. Inhibition of low density lipoprotein (LDL) oxidation by l-deprenyl in a dose dependent manner. LDL isolated from a male subject was incubated with varying concentrations of l-deprenyl. Diene formation is a measure of LDL oxidation. For details see Thomas et al; Neurol. Res. 2002, 24: 169-173.

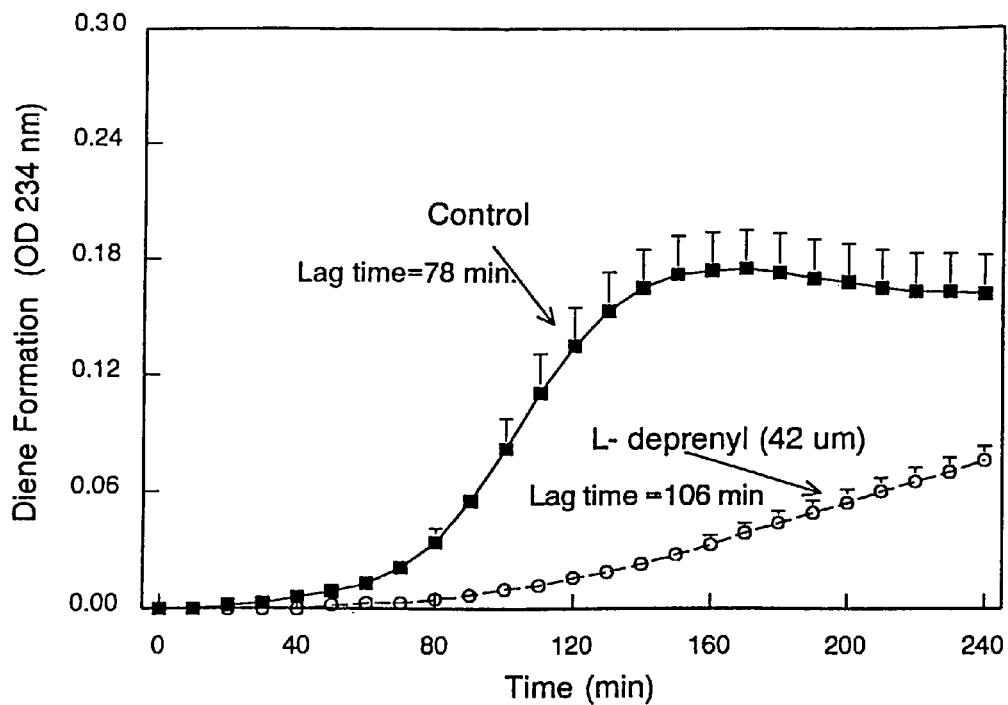
Figure 8. Inhibition of low density lipoprotein (LDL) oxidation by l-deprenyl. LDL isolated from postmenopausal women was incubated with l-deprenyl. Diene formation is a measure of LDL oxidation. For details see Thomas et al; Neurol. Res. 2002, 24: 169-173.

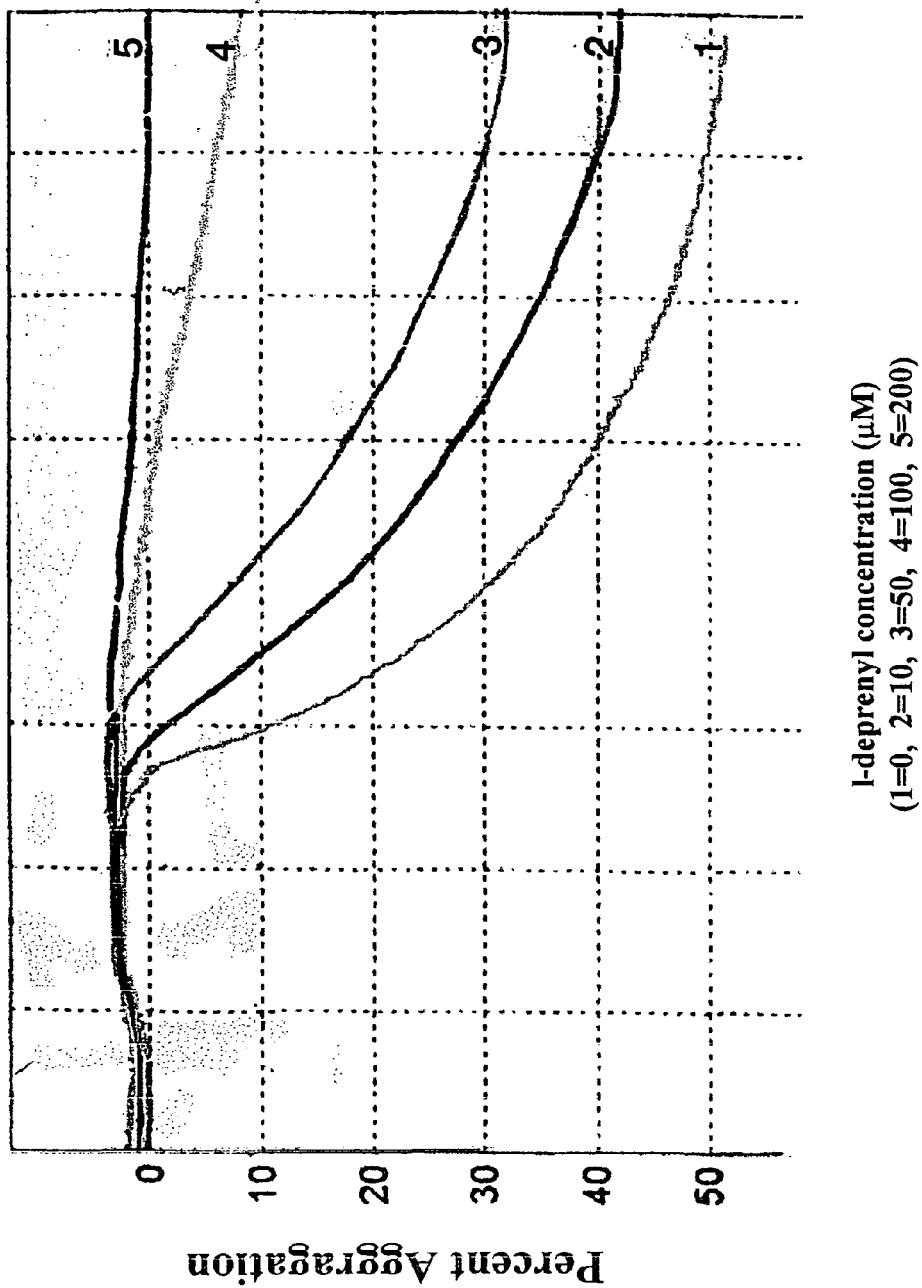
Figure 9. Inhibition of human platelet aggregation by l-deprenyl

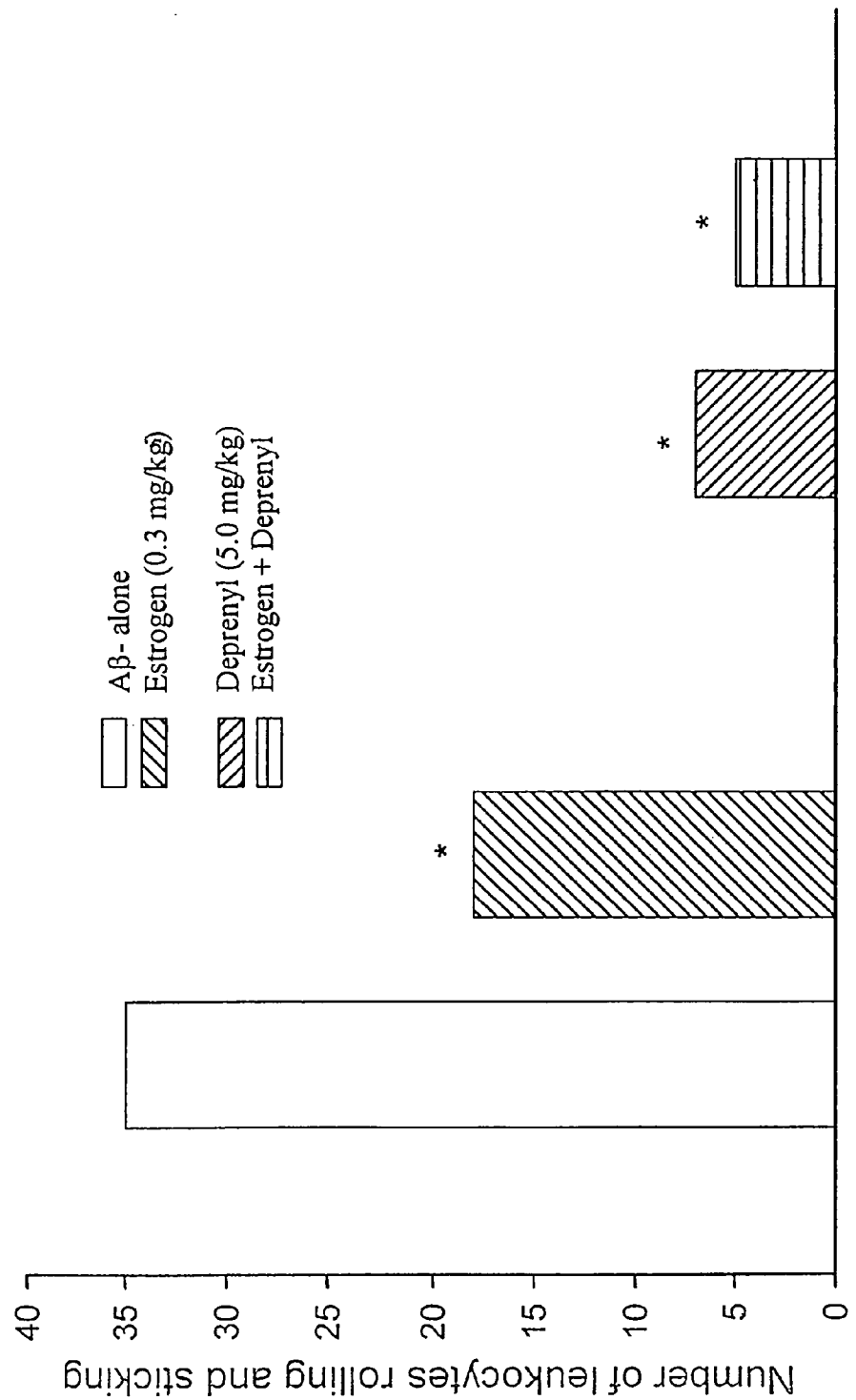
Figure 10. Inhibition of inflammatory reaction by l-deprenyl

METHODS AND COMPOSITIONS TO ENHANCE THE EFFICACY OF PHOSPHODIESTERASE INHIBITORS

RELATED APPLICATION

This application is continuation-in-part of Ser. No. 09/881,199, filed Jul. 27, 2000, now U.S. Pat. No. 6,432,991, Ser. No. 09/927,982, filed Aug. 10, 2001, now U.S. Pat. No. 6,635,337, U.S. patent application Ser. No. 10/802,000, filed Mar. 16, 2004 and U.S. provisional application No. 60/486,121, filed Jul. 11, 2003 the entire contents of which are hereby incorporated by reference.

FIELD OF THE INVENTION

This invention relates to methods of treating sexual dysfunction. Methods of using combinations of phosphodiesterase inhibitors and l-deprenyl or propargylamine compounds (also known as monoamine oxidase inhibitors) in the treatment of erectile dysfunction and other diseases are also provided.

STATEMENT REGARDING FEDERAL SPONSORED R & D

No federal, state, or other government funding was used to develop this patent.

BACKGROUND OF THE INVENTION

Normal sexual function involves a complex interaction of emotional, neuronal, vascular and hormonal factors. In addition sexuality incorporates personal, family, social and religious beliefs and is altered with aging, health status, and personal experience (Tomlinson, 2004).

A disruption in any of these areas may lead to sexual dysfunction. Sexuality in females may particularly involve many brain-mediated responses. About 43 percent (40 million) women in the US experience some form of sexual dysfunction. Sexual dysfunction in a female may include hypoactive sexual desire disorders, arousal disorders, orgasmic, or sexual pain disorders. Physical and emotional stimulation lead to breast and genital vasodilation and clitoral engorgement. In the female, dilation and engorgement of the blood vessels in the labia and tissue surrounding the vagina produce an orgasmic response.

Male sexual dysfunction may include erectile dysfunction and impotence. Erectile dysfunction (ED) in the male is defined as the inability to maintain an erect penis with sufficient rigidity to allow sexual intercourse. Erectile dysfunction is a common problem affecting about 30 million men in the US (NIH, 1993). It is estimated that the world-wide incidence of ED will increase from 152 million in 1995 to 322 million men by the year 2025 (Ayta et al; 1999).

It is an age-related condition with about 39% of men over 40 and 67% of men over 70 years suffering from erectile dysfunction (Seftel, 2003). Many conditions such as atherosclerosis can reduce blood flow to the penis, causing ED. Other conditions such as diabetes, hypertension, hyperlipidemia, and cigarette smoking also will lead to ED. Normal erection is mediated through the central nervous system which transmits psychogenic and sensory stimuli to the sympathetic nervous system which controls penile blood flow (Steif, 2003). The arterial blood vessels dilate and deliver blood to the penis, which enables the corpora cavernosa sinus system to become engorged with blood. Vasodilation of the cavernosal arteries and closure of the venous drainage in the penis produce an erection. The hypothalimic-pituitary-testicular axis also has a role as testosterone is required for normal libido (Rhoden, 2002).

Any psychological, neurologic, vascular, urogenital and endocrine abnormality may cause erectile dysfunction. Diabetes is one of the most common causes of ED (DeAngelis, 2001; Utkan, 2001). Other factors leading to ED are smoking, vascular disease, atherosclerosis, hypertension (Burchardt, 2000), hypercholesterolemia, renal failure, injury, surgery, hypogonadism and drugs. A variety of drugs can initiate and accelerate erectile dysfunction (Galle, 2003). These drugs include antihypertensives like beta adrenoreceptor blockers, diuretics, digoxin, antidepressants and antipsychotics, histamine-2 receptor antagonists, alcohol, opiates, amphetamines, and cocaine.

About 80% of patients with ED develop the condition because of a drug or some organic illness. The remaining 20% have a primary psychogenic cause (Rosen, 2001). Psychogenic ED may be treated with behavioral therapy (DeBeradis, 2003), which is successful in half of the patients. If ED is due to organic illness, or if it is psychogenic, but cannot be corrected by behavioral therapy, drug therapy is used (Galle, 2003; Carson 2000).

Current Methods for Treatment of ED

1. Vacuum constriction devices suitable for patients with venous disorders (Dutta 1999).
2. Prosthetic devices which are directly implanted into paired corporal bodies. These devices may be rigid, malleable, hinged, or inflatable.
3. Vascular reconstructive surgery is used for patients with disorders of the arterial system.
4. Testosterone (injection or skin patches) can be used for men with documented androgen deficiency. Men with prostatic cancer or elevated PSA should not be given testosterone.
5. Direct injection of prostaglandin E1 (alprostadil) into the penis. Common side effects are dizziness, local pain, fibrosis, and infection (Chiang, 2000).
6. Drugs like apomorphine, dopamine receptor agonists, phentolamine, yohimbine, papaverine, vasoactive intestinal peptide, melanocortin receptor agonists, and combinations of these drugs (Carson 2000; Goldstein 2000).
7. Phosphodiesterase (especially type 5) inhibitors (McMahon, 2000).

Phosphodiesterase Inhibitors

Phosphodiesterase (PDE) inhibitors are a class of intracelleular enzymes which mediate the catabolism of second messengers like cyclic adenosine monophosphate (cAMP) and cyclic guanosine monophosphate (cGMP). These enzymes have been classified into at least eleven groups (types I-XI) and various subclasses based on their amino acid sequence and substrate specificity (Polson, 1996; Trophy, 2000). The various PDE differ in their tissue, cellular distribution, and their specificity towards cAMP or cGMP. (table 1). So phosphodiesterase inhibitors have applications in a number of disorders including vascular, neuronal and inflammatory disorders (Zang 2002, Martin 2002, Grootendorst 2002, Burnouf, 2002). PDE inhibitors are drug candidates for the treatment of a number of disorders including heart failure, depression, asthma, inflammation, sexual dysfunction, and erectile dysfunction. Phoshodiesterase 4D has been shown to have a role in ischemic stroke (Gretarsdottir, 2003).

TABLE 1

Human Phosphodiesterases (PDE)

| Specificity | PDE type | Tissue localization | Disorder | Inhibitors |
|---|---|---|---|---|
| cAMP | 3 | Heart, corpus cavernosum, platelets, smooth muscle (vascular, visceral, bronchial), vagus nerve, liver, kidney endothelium, lymphocyte, mast cell | | Enoximone, piroximone olprinone, motapizone, milrinone, amrinone, cilostamide, cilostazol |
| | 4 | Kidney, lung, heart, skeletal muscle, smooth muscle (vascular, visceral, airway), endothelium, inflammatory cells, platelets, vagus nerve | Inflammatory disorders depression allergy, asthma stroke | Rolipram, piclamilast tibenelast, benafentrine zardaverine, tolafentrine |
| | 7 | Skeletal muscle, heart, kidney, airways, lymphocytes, monocyte eosinophil | | Dipyridamole |
| | 8 | Testis, ovary, ileum, colon, heart, brain, kidney, pancreas, airways, monocyte, thyroid | | Dipyridamole |
| cGMP | 5 | Corpora cavernosa, platelets, skeletal muscle, smooth muscle (vascular, visceral, airway), kidney, vagus nerve | Erectile dysfunction female sexual dysfunction, pulmonary hypertesion Impotence | Sildenafil, Tadalafil Vardenafil zaprinast, dipyridamole papavenne |
| | 6 | Retina (rods and cones) | | PDE 5 inhibitors |
| | 9 | Spleen, small intestine, brain | | Zaprinast |
| cAMP & cGMP | | Heartt, brain, kidney, liver, skeletal muscle, smooth muscle (vascular, visceral, airway), vagus nerve | | MIMX, vinpocetine phenothiazines |
| | 2 | Adrenal cortex, brain, heart, liver, corpus cavernosum, platelet, airway smooth muscle | | EHNA (erytro-9-[2-hydroxyl] adenine) |
| | 10 | Brain (putamen, caudate nucleus) | | IBMX |
| | 11 | Skeletal muscle, prostate, kidney, liver, pituitary, salivary glands, testis | | zaprinast dipyridamole |

Nitric Oxide and Erectile Dysfunction

Nitric oxide (NO) formed from L-arginine by the enzyme nitric oxide synthase (NOS) is the prime mediator of endothelium-dependent smooth muscle relaxation and penile erection (Burnett, 1992). NO regulates vascular tone and promotes blood vessel relaxation and also has other roles in immune system, nervous system, and inflammation. NO is synthesized and released by neuronal (nNOS) and endothelial (eNOS). Both eNOS and nNOS are constitutively expressed in the endothelium and penile nerve endings (Hedlund, 2000; Bloch, 1998). Upon sexual stimulation NO is released from nerve endings, or from endothelial cells stimulated by acetylcholine from cholinergic nerve endings (Lue, 2000). It is likely that penile erection is mediated by both nNOS and eNOS. Reduced androgen levels, found in elderly men cause impaired expression of penile NO synthesis. NO synthesis is also impaired by hypertension, high levels of oxidized LDL, TNF alpha, and cAMP. NO activates a soluble guanyl cyclase that forms cyclic guanosine mononphosphate (cGMP). Cyclic GMP is the primary second messenger that mediates penile erection. Phosphodiesterase 5 inhibitors like sildenafil prevents the degradation of cGMP and enhances erectile function. NO activates prostaglandin synthesis. The prostacyclin thus formed along with NO released by eNOS and nNOS stimulation causes relaxation of smooth muscle cells. Impaired NOS function, rather than NOS expression is considered to be the cause of insufficient NO production and the inability to stimulate the penile corpora cavernosa to elicit a normal erectile response Gonzalez-Cadavid, 2000; Maas, 2003). Prostaglandin E1 and its derivative alprostadil, which induce relaxation mainly through cAMP also enhance erection (Porst, 1996).

Inflammatory processes cause a shift from vasodilatory to vasoconstrictor eicosanoids. Under such conditions NO generated from eNOS and nNOS is not sufficient to cause smooth muscle relaxation.

Oxidative stress contributes to the development of atherosclerosis, endothelial dysfunction, and ED. By reacting with NO itself, or by interfering with NO-mediated pathways, reactive oxygen species (ROS) could contribute to erectile dysfunction. Thus antioxidants will enhance erectile function by scavenging ROS and enhancing bioavailability of NO.

Examples of type V (5) phosphodiesterase inhibitors include, but not limited to, sildenafil, tadalafil, vardenafil, avanafil, Zaprinast®, papaverine and dipyridamole. Other type 5 PDE inhibitors are disclosed in PCT Publication Nos. WO 94/28902, WO 96/16644, U.S. Pat. No. 6,338,862 and U.S. Pat. No. 6,476,037.

Other Potential Applications of PDE5 Inhibitors
1. Enhance sexual function in men following prostate surgery.
2. Enhance sexual function in hypogonadal men by combining testosterone and PDE inhibitor.
3. Treatment of premature or rapid ejaculation.
4. Enhance sexual function in women
5. Enhance endothelial function in patients with primary pulmonary hypertension.
6. Treatment of urinary tract symptoms due to benign prostatic hyperplasia.
7. Treatment of urinary incontinence.
8. Treatment of sickle cell anemia by combination therapy with hydroxyurea
9. Enhance sexual function in men and women by combination therapy with antioxidants, vitamin E, arginine, apomorphine , dopamine agonists, alpha adrenergic blocker etc.
10. Prevention and treatment of stroke.
11. Treatment of coronary and cerebral vascular diseases.
12. Treatment of thrombosis
13. Treatment of ocular hypertension
14. Treatment of pregnancy-induced hypertension.
15. Treatment of anal sphincter disorders (Jones, 2002).
16. Treatment of neurodegenerative diseases such as Alzheimer's disease, Parkinson's disease, amyloid diseases, Prion diseases.
17. Treatment of other diseases where cGMP is implicated to have beneficial effects.

Side Effects and Complications of PDE5 Inhibitors

The side effects of PDE inhibitors include hypotension, flushing, headache, nasal congestion and heartburn and these effects are dose dependent (Moreira, 2000). The incidence of cardiovascular events and deaths have been reported with the use of PDE 5 inhibitors (Lim, 2002). This may be due to the fact that PDE5 inhibitors dilate the coronary arteries which makes the patient feel better. This may lead to vigorous physical activity (exercise or intercourse). Such activity may lead to ischemia and heart attack. Also interaction with other drugs including nitroglycerine poses substantial risks. The visual side effects of PDE 5 inhibitors are due to the inhibition of PDE 6 found in the retina. Currently available therapies for ED are palliative, have significant failure rates and side effects, and require treatment prior to each sexual encounter. So novel methods of treatment for patients unresponsive to current treatments are required. In ED, the activity of penile NOS is reduced, or the NO synthesis is not sufficient to produce a normal erectile response. Therefore, stimulation of penile NO synthesis seems to be the ideal treatment for ED. Use of synthetic NO donor compounds have not proved successful due to poor stability and delivery problems of these compounds. Enhancing NO synthesis by administration of the substrate L-arginine is another approach. But the availability of L-arginine is not a rate-limiting step for NOS. Administration of massive doses of L-arginine for long-term is necessary to produce any detectable increase in NO production. This invention describes a practical and efficient method for stimulation of nitric oxide production and enhancing the efficacy of PDE 5 inhibitors in the treatment of ED and other disorders.

Brain mechanisms, particularly activation of dopamine receptors play a major role in normal sexual function (Giuliano, 2001). PDE 5 inhibitors have no effect on brain dopamine activity. Apomorphine and other agents that enhance dopamine also enhance erectile function (Stief, 2003). But these dopaminergic drugs do not enhance penile blood flow. Deprenyl and other MAO inhibitors elevate dopamine levels in the brain and thus can augment sexual function (Knoll, 1989).

Deprenyl and other propargylamine compounds will enhance the efficacy of PDE 5 inhibitors by several mechanisms including stimulation of nitric oxide production and enhanced dopamine activity.

SUMMARY OF THE INVENTION

Detailed Description of the Invention

The present invention is based on the discovery that a selective group of compounds, l-deprenyl and propargylamine compounds (monoamine oxidase [MAO] inhibitors), acts synergistically with type 5 phosphodiesterase inhibitors to induce vasodilation and or prevent vasospasm.

Phosphodiesterase type 5 inhibitors potentiate the actions of nitric oxide (NO) by elevating the levels of CGMP, and thus enhance blood flow and erectile function. We have previously shown that l-deprenyl and propargylamine compounds stimulate the production of nitric oxide both in peripheral and cerebral tissues (Thomas, 2001, 1998; U.S. Pat. No. 6,432, 991). MAO inhibitors also elevate the levels of dopamine, a key mediator of sexual function in the brain. We show here that MAO inhibitors augment the actions of PDE5 inhibitors, reduce side effects, and enable the reduction of the dose of PDE inhibitors.

The flow chart below illustrates sites of actions of these compounds.

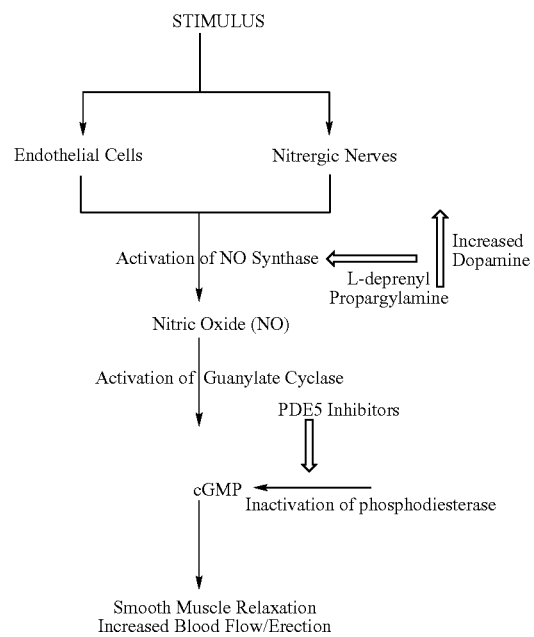

It has been shown that l-deprenyl and other propargylamine derivatives induce, NO production, vasodilation, and endothelial protection (Thomas, 2001, 1998). These compounds will act synergistically with PDE inhibitors. Thus l-deprenyl like compounds may be useful in augmenting the effects of inhibitors of various classes of PDE inhibitors.

The beneficial actions of l-deprenyl and propargylamine compounds may also be mediated by the following actions— nitric oxide production, vasodilation, endothelial protection, smooth muscle relaxation, antioxidant action, free radical scavenging, antiapoptotic action, stimulation of antioxidant enzymes, anti-inflammatory activity, monoamine oxidase inhibition, enhanced dopamine activity, inhibition of phosphodiesterase, enhancement of monoamine activity, neuroprotection, antidepressant, antidiabetic, etc. (Thomas, 2001, 1998;-Maia, 2004). In addition l-deprenyl may enhance sexual function by elevating dopamine levels in the brain through MAO-B inhibition.

The synergestic effect of type 5 PDE inhibitors and l-deprenyl or propargylamine compounds can be utilized in a number of conditions. In one preferred embodiment, combinations of l-deprenyl and one or more PDE5 inhibitors are administered to a male subject to treat erectile dysfunction and other sexual disorders. In another preferred embodiment, combinations of l-deprenyl and PDE5 inhibitors are administered to a female subject to treat sexual dysfunction. In another preferred embodiment, combinations of l-deprenyl and PDE5 inhibitors are administered to a subject to prevent or reduce vasospasm of a coronary artery or bypass graft. In another preferred embodiment, combinations of l-deprenyl and PDE5 inhibitors are administered to produce vasodilation.

In another preferred embodiment, combinations of l-deprenyl and PDE5 inhibitors are administered to a subject to prevent or treat conditions such as:

Sexual dysfunction in men following prostate surgery.

Sexual dysfunction in hypogonadal men by combining testosterone and PDE inhibitor.

Premature or rapid ejaculation.

Sexual dysfunction in women

Endothelial dysfunction in patients with primary pulmonary hypertension.

Urinary tract symptoms due to benign prostatic hyperplasia.

Urinary incontinence.

Sickle cell anemia by combination therapy with hydroxyurea.

Sexual dysfunction in men and women by combination therapy with antioxidants, vitamin E, arginine, apomorphine, beta blocker, or alpha adrenergic blockers.

Monoamine oxidase inhibitors contemplated in the invention include l-deprenyl (selegiline), r-deprenyl, desmethyl selegiline, clorgyline, pargyline, iproniazid, nialamide, phenelzine, tranylcypromine, quinacrine, hydrazine, carboxamide, RO 16-6491, RO 41-1049, propargylamines (eg. Rasagiline, Lazabemide), N-propargylamine compounds, N-methyl propargylamine, and N-methyl-N-(2-pentyl)-propargylamine. Other MAO A and B inhibitors, both natural and synthetic are also contemplated. Chemical modifications, derivatives and metabolites of MAO inhibitors, both natural and synthetic are also contemplated in the invention. Compounds of the invention with one or more asymmetric carbon atoms may exist as enantiomers, diastereomers or as racemic mixtures, it is to be understood that the present invention anticipates and includes within its scope such isomers and mixtures.

Phosphodiesterase inhibitors contemplated in the invention include type 5 phosphodiesterase inhibitors such as, but not limited to, sildenafil, tadalafil, vardenafil, avanafil, zaprinast, dipyridamole, propentofylline, papverine, IBMX, pyrazolopyrimidinones, griseolic acid derivatives, 2-phenylpurinones, phenylpyridone derivatives, pyrimidines, purines, quinazolines, phenylpyrimidinones, imidazoquinoxalinones, phenylpyridones, 4-bromo-5-(pyridylmethylamino)-6-[3-(4-chlorophenyl)propoxy]-3(2H)pyridazinone, 1-[4-[(1,3-benzodiozol-5-9pyridylmethylamino)-6-chloro-2-quinazolinyl]-4-piperidine-carboxylic acid, (+)-cis-5,6a,7,9,9,9a-hexahydro-2-[4-(trifloromethyl)-phenylmethyl-5-methyl cyclopent-4,5]imidazo[2.1-b]purin-4(3H)one, furazlocillin, cis-2-hexyl-5-methyl-3,4,5,6a,7,8,9,9a-octahydrocyclopent[4,5]imidazo[2,1-b]purin-4-one, 3-acetyl-1-(2-chlorobenzyl)-2-propylindole-6-carboxylate, 4-bromo-5-(3-pyridylmethylamino)-6-(3-(4-chlorophenyl)propoxy)-3(2H) pyridazinone, 1-methyl-5-(5morpholinoacetyl-2-n-propoxyphenyl)-3-n-propyl-1,6-dihydro-7H-pyrazolo(4,3-d) pyrimidin-7-one, 1-[4[(1,3-benzodioxol-5-methyl)amino]-6-chloro-2-quinazolinyl]4-piperidine carboxylic acid. Salts, derivatives and metabolites of phosphodiesterase 5 inhibitors are also included. Other type 5 PDE inhibitors are disclosed in PCT Publication Nos. WO 94/28902, WO 96/16644, U.S. Pat. No. 6,338,862 and U.S. Pat. No. 6,476,037.

The optimal doses MAO inhibitor in a pharmaceutical composition is in the amounts of 0.1 to 100-mg/kg body weight and the doses of MAO inhibitors in the pharmaceutical composition may be in the amounts of 0.1-50.0 mg/kg. Depending on the application, the optimal doses of PDE5 inhibitors will vary from 0.1 mg to 500 mg. It is also contemplated that compounds of the invention will also enhance the actions of other PDE inhibitors, more specifically type I, II, III, IV, VI, and VII.

It is also contemplated that compounds of the invention will enhance the effects of other modalities of treatment for erectile dysfunction. More specifically these modalities include psychotherapy, surgical methods, implants, and vacuum methods.

Pharmaceutical Formulations and Modes of Administration

According to this invention, one or more of PDE5 inhibitors are administered in conjunction with l-deprenyl or propargylamine compounds to an individual prone to erectile dysfunction and or other conditions listed previously. While this invention is described in terms of application to human subjects, veterinary applications are contemplated within the scope of this invention. The PDE inhibitor and l-deprenyl can be administered simultaneously or sequentially. Both PDE inhibitor and l-deprenyl can be administered by the same modality (in the same preparation) or they can be administered in different formulations and/or by different modalities.

The PDE inhibitors, and or l-deprenyl may be administered in the form of salts, esters, amides, prodrugs, derivatives and may be prepared using standard procedures known to those skilled in the art.

Type 5 PDE inhibitors and l-deprenyl may be administered as parenteral, topical, oral, or local administration such as by aerosol or transdermally, for prophylactic and/or therapeutic treatment of erectile dysfunction and other conditions. The pharmacological compositions can be administered in a variety of unit dosage forms or kits depending upon the method of administration. Suitable unit dosage forms include, but are not limited to powders, tablets, capsules, injectibles, lozenges, creams, suspensions, suppositories, etc. The concentration of active ingredients in the formulation can vary and will be based on the nature and extent of the disease, body weight, or fluid volumes in accordance with the needs of the subject.

BRIEF DESCRIPTION OF THE DRAWINGS

The following examples illustrate various actions of MAO inhibitors which enhance the biological actions of phosphodiesterase inhibitors, but do not limit the scope of the invention in any way. Further aspects of the invention, based on the disclosure above and the following examples, will be apparent to the person of ordinary skill in the art.

EXAMPLE 1

Enhancement of Dilation of Rabbit Corpus Cavernosa Smooth Muscle by l-deprenyl

FIG. 1 illustrates the enhanced relaxation of rabbit corpus cavernosa by l-deprenyl in a dose dependent manner. The phosphodiesterase 5 inhibitor sildenafil had no detectable effect on dilation. Low concentrations of l-deprenyl stimulated the relaxation of corpus cavernosa and would thus enhance erectile function.

EXAMPLE 2

Enhancement of Sildenafil Action by l-deprenyl, Mediated by Nitric Oxide

FIG. 2 demonstrates that l-deprenyl enhances the dilation of corpus cavernosa by sildenafil. The inhibition of this effect by hemoglobin (an agent that traps nitric oxide), indicates that the effect of l-deprenyl is mediated by nitric oxide.

EXAMPLE 3

Enhancement of Dilation of Rabbit Corpus Cavernosa by l-deprenyl Involves cGMP

FIG. 3 demonstrates that l-deprenyl enhances the dilation of corpus cavernosa by sildenafil. The inhibition of this effect by methylene blue (an agent that inhibits cGMP formation), indicates that the effect of l-deprenyl is mediated by increased production of cGMP.

EXAMPLE 4

Enhancement of Dilation of Rabbit Corpus Cavernosa in l-deprenyl Treated Animal

Rabbits were treated orally with 1 mg/kg of l-deprenyl orally. The relaxation of the isolated corpus cavernosa was measured as described under methods. L-deprenyl treated animal showed significantly enhanced relaxation. Inhibition of l-deprenyl effect by methylene blue (FIG. 4) indicates that cGMP mediates this action.

EXAMPLE 5

Enhancement of Dilation of Rabbit Corpus Cavernosa by Dipyridamole

The phosphodiesterase 5 inhibitor dipyridamole produced minimal dilation of rabbit cavernosa, The effect of dipyridamole was enhanced by l-deprenyl (FIG. 5). This illustrates that l-deprenyl is capable of enhancing the actions of different phosphodiesterase inhibitors.

EXAMPLE 6

Enhancement of Dilation of Corpus Cavernosa from Diabetic Animal by l-deprenyl

Vascular dysfunction in diabetic state increases the risk for erectile dysfunction. Corpora cavernosa smooth muscle were isolated from 8 week diabetic rabbits Diabetes was induced in rabbits using alloxan. These animals showed a decreased vasodilatory response (FIG. 6). Addition of l-deprenyl enhanced the dilation of corpus cavernosa from diabetic animals by sildenafil. Thus l-deprenyl-like compounds will be effective in treating vascular dysfunction in diabetes.

EXAMPLE 7

Inhibition of Human Low Density Lipoprotein (LDL) Oxidation by l-deprenyl

Oxidized LDL accelerates atherosclerosis and contributes to the pathology of ED. FIGS. 7 and 8 show that l-deprenyl inhibits human LDL oxidation. So l-deprenyl and other MAO inhibitors will be effective in the prevention and treatment of ED and other vascular disorders.

EXAMPLE 8

Inhibition of Human Platelet Aggregation by l-deprenyl

Platelet aggregation has a major role in the development of atherosclerosis and thrombosis, contributing to endothelial dysfunction and ED. FIG. 9 shows that l-deprenyl inhibited the aggregation of human platelets in a dose-dependent manner. Inhibition of platelet inhibition will ameliorate ED and other vascular disorders.

EXAMPLE 9

Antiinflammatory Activity of l-deprenyl

Leukocyte rolling and migration is a measure of inflammatory reaction, which is an early event in atherosclerosis and ED. The anti-inflammatory action of estrogen was potentiated by l-deprenyl as shown in FIG. 10. Thus l-deprenyl will retard the development and progression of ED and other vascular disorders.

DISCUSSION

The results of these examples clearly indicate that, under the conditions tested, the monoamine oxidase inhibitor compounds like l-deprenyl produce dilation of corpus cavernosa and also enhance the effect of phosphodiesterase 5 inhibitors. These actions of MAO inhibitors are mediated through increased production of nitric oxide and cGMP. Other actions of MAO inhibitors which contribute to this effect are also described. Therapeutic methods of using MAO inhibitors and phosphodiesterase inhibitors for the treatment of erectile dysfunction, other male sexual disorders, female sexual disorders, and a variety of vascular, cerebral and peripheral disorders are disclosed. The ratio of MAO inhibitors and phosphodiesterase inhibitors used for these applications can be varied depending on the nature and severity of the disorder, and the affected tissue or organ.

Having now fully described the invention, it will be appreciated by those skilled in the art that the same can be performed within a wide range of equivalent parameters, concentrations and conditions without departing from the spirit and scope of the invention and without undue experimentation.

While the invention has been described in detail with respect to particular preferred embodiments, it should be understood that such description is presented by way of illustration and not limitation. Many changes and modifications within the scope of the present invention may be made without departing from the spirit thereof, and the invention includes all such modifications.

All references cited herein, including journal articles or abstracts, published or corresponding U.S. or foreign applications, or any other references are entirely incorporated by reference herein, including all data, tables, figures, and text presented in the cited references. Additionally, the entire contents of the references cited within the references cited herein are also entirely incorporated by references.

Reference to known methods, steps, or conventional methods, is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not limitation, such that the terminology or phraseology of the present specification is to be interpreted by the skilled artisan in light of the teachings and guidance presented herein, in combination with knowledge of one of ordinary skill in the art.

REFERENCES

Abrams D. et al. (2000) Sidenafil as a selective pulmonary vasodilator in childhood primary pulmonary hypertension. Heart 84: E4.

Ayta J A, et al. (1999) The likely worldwide increase in erectile dysfunction between 1995 and 2025 and some possible policy consequences. BJU Int. 84: 50-56.

Ballard (1998) effects of Sildenafil on the relaxation of human corpus cavernosum tissue in vitro and on the activities of cyclic nucleotide phosphodiesterase isozymes. J. Urology. 159: 2164-2171.

Beshav E; Prud'homme G J. (2001) Inhibitors of phosphodiesterase isoforms 3 or 4 suppress islet cell nitric oxide production. Lab Invest. 81: 1109-1117.

Bloch W. et al.(1998). Evidence for the involvement of endothelial nitric oxide synthase from smooth muscle cells in the erectile function of the human corpus cavernosum. 26: 129-135.

Burchardt M. et al. Hypertension is associated with severe erectile dysfunction. J. Urol. 164: 1188-1191.

Burnett A L. et al. (1992).nitric oxide: a physiologic mediator of penile erection. 257: 401-403.

Burnouf C; Pruniaux M P. (2002) Recent advances in PDE4 inhibitors as immunoregulators and anti-inflammatory drugs. Curr. Pharm. Des. 8: 1255-1296.

Bush et al. (1992) Nitric oxide is a potent relaxant of human and rabbit corpus cavernosum. J. Urology. 147: 1650-1655.

Carson C C. (2000) Oral and injectible medications for treatment of erectile dysfunction. Curr. Urol. Rep. 1: 307-312.

Chiang H S. et al. (2000) Titration study of MUSE (medicated urethral system for erection) in erectile dysfunction. J. Formos. Med. Assoc. 99: 926-930.

DeAngelis L. et al. (2001) Erectile and endothelial dysfunction in Type 2 diabetes: a possible link. Diabetologia 44: 1155-1160.

DeBerardis G. et al (2003) Identifying patients with type 2 diabetes with a higher likelihood of erectile dysfunction: the role of the interaction between clinical and psychological factors. J. Urol. 169: 1422-1428.

Dutta T C; Eid J F. (1999) Vacuum constriction devices for erectile dysfunction: a long-term, prospective study of patients with mild, moderate and severe erectile dysfunction. Urology 54: 891-893.

Galle G. and Trummer H. (2003). The etiology of erectile dysfunction and mechanisms by which drugs improve erection. Drugs of Today, 39: 193-201.

Giuliano F. (2001) Dopamine and sexual function. Eur. Eurol. 40: 601-608.

Goldstein I (2000) Oral Phentolamine: an alpha-1, alpha-2 adrenergic antagonist for the treatment of erectile dysfunction. Int. J. Impot. Res. 1: S75-80.

Gonzalez-Cadavid N F. And Rajfer J. (2000) Therapeutic stimulation of penile nitric oxide synthase and related pathways. Drugs of Today. 36: 163-174.

Gretarsdottir S, Thorieifsson G, Reynisdottir S Th, et al, (2003) The gene encoding for phosphodiesterase 4D confers risk of ischemic stroke. Nature 35: 131-138.

Grootendorst D C, Rabe K F. (2002) Selective phosphodiesterase inhibitors for the treatment of asthma and chronic obstructive pulmonary disease. Curr. Opin. Allergy Clin. Immunol. 2: 61-67.

Hedlund P. et al. (2000) Cholinergic nerves in human corpus cavernosum and sponigiosum contain nitric oxide synthase and heme oxygenase. J. Urol. 164: 868-875.

Jackson et al. (1999) effects of sildenafil citrate on human hemodynamics. Am. J. Cardiol. 83: 13C-20C.

Jones O M et al. ((2002) Phosphodiesterase inhibitors cause relaxation of the internal anal sphincter in vitro. Dis. Colon Rectum 45: 530-536.

Knoll J. (1989) Striatal dopamine, sexual activity and life span. Longevity of rats treated with deprenyl. Life Sci. 45: 525-531.

Lue T F (2000) Erectile dysfunction. N. Engl. J. Med. 342: 1802-1813.

Maas R. et al (2003) The pathophysiology of erectile dysfunction related to endothelial dysfunction and mediators of vascular function. Vascular Medicine 7: 213-225.

Maia F D. et al. (2004) l-deprenyl prevents lipid peroxidation and memory deficits produced by cerebral ischemia in rats. Cell Mol Neurobiol. 24: 87-100.

Martin C. et al (2002). Airway relaxant and anti-inflammatory properties of PDE4 inhibitor with low affinity for the high-affinity rolipram binding site. Naunyn Schmiedebergs Arch. Pharmacol. 365: 284-289.

McMahon C G. et al. (2000). Efficacy, safety and patient acceptance of sildenafil citrate as a treatment for erectile dysfunction. J. Urol. 164: 1192-1196.

Mitka M. (2003) Researchers seek new uses for sildenafil. JAMA 289: 2784-2786.

Moreira S G. Et al. (2000) Side-effect profile of sildenafil citrate (viagra) in clinical practice. Urology 56: 474-476.

NIH concensus development panel on impotence (1993). NIH concensus conference: impotence. JAMA, 270: 83-90.

Polson (1996) Cyclic nucleotide phosphodiesterases and vascular smooth muscle. Annual Review of Pharmacol. 26: S13-S20.

Porst H. (1996) The rationale for prostaglandin E1 in erectile failure: a survey of worldwide experience. J. Urol. 155: 802-815. Porst H. (1996) The rationale for prostaglandin E1 in erectile failure: a survey of worldwide experience. J. Urol. 155: 802-815.

Rajfer et al (1992). Nitric oxide is a mediator of relaxation of the corpus cavernosum in response to noradrenegic, noncholinergic neurotransmission. NEJM 326: 90-94

Rhoden, E L. Et al (2002) The relationship of serum testosterone to erectile function in normal aging men. J. Urol. 167: 1745-1748.

Rosen R C. (2001) Psychogenic erectile dysfunction. Classification and management. Urol. Clin. North Am. 28: 269-278.

Sebkhi A. et al. (2003) Phosphodiesterase type 5 as a target for the treatment of hypoxia-induced pulmonary hypertension. 107: 3230.

Seftel, A D. (2003) Erectile dysfunction in the elderly: epidemiology and approaches to treatment. J. Urol. 169: 1999-2007.

Stief C G. (2003). Central mechanisms of erectile dysfunction: what a clinician may want to know. Int. J. Impot. Res. Suppl. 2: S3-S6.

Sung B-J. et al. (2003) Structure of the catalytic domain of human phosphodiesterase 5 with bound drug molecules. Nature 425: 98-102.

Thomas, T. (2002) Methods of treatment using MAO-A and MAO-B inhibitors such as l-deprenyl. U.S. Pat. No. 6,432,991

Thomas, T. (2000) Monoamine oxidase-B inhibitors in the treatment of Alzheimer's disease. Neurobiol. Aging. 21: 343-348.

Thomas T (2001) A role for estrogen in the primary prevention of Alzheimer's disease. Climacteric. 4: 102-109.

Thomas T, et al. (2002) Inhibition of LDL oxidation by the neuroprotective drug l-deprenyl. Neurol. Res. 24: 169-173.

Thomas T. et al. (1998) L-deprenyl: nitric oxide production and dilation of cerebral blood vessels. NeuroReport. 9: 1-6.

Thomas T. et al. (1998) L-deprenyl protects vascular endothelium from amyloid-beta toxicity and stimulates production of nitric oxide. In Alzheimer's disease and related disorders. (Ed. Iqbal K. et al.) pp 493-500, John Wiley and Sons Ltd.

Tomlinson J and Wright D. (2004) Impact of erectile dysfunction and its subsequent treatment with sildenafil: qualitative study. Brit. Med. J. 328: 1037.

Trophy, T J; Page C. (2000) Phosphodiesterases: the journey towards therapeutics. Trends in Pharmacol. Sci. 21: 157-169.

Utkan, T. et al (2001) Effects of specific phosphodiesterase inhibitors on alloxan-induced diabetic rabbit cavernous tissue in vitro. Int. J. Impot. Res. 13: 24-30.

Zang B et al. (2002) Suppressive effect of phosphodiesterase type 4 inhibitors on rat cultured microglial cells: comparison with other types of cAMP-elevating agents. Neuropharmacology 42: 262-269.

METHODS

1. Induction of Diabetes

New Zealand white rabbits (body weight 3.0 kg) were injected intravenously with alloxan (via the lateral ear vein) at a standard dose of 65 mg/kg. Urine was monitored over the duration of diabetes for glucose, ketone bodies and proteins.

1. Preparation of Penile Tissue

After 6 months of alloxan treatment, rabbits (together with age matched controls) were killed by cervical dislocation and penises were excised and placed in DMEM pre-gassed with 95% oxygen and 5% carbon dioxide. Epidermal and connective tissue, urethra and corpus spongiosum were carefully excised from the penis. The corpora cavernosa was then cut longitudinally into two equal segments and then transversely into segments (approx. 2 mm×2 mm×10 mm).

2. Organ Chamber Experiments

Strips of corpus cavernosum were studied in 10.0 mL organ chambers for isomtric tension measurement. The strips were tied with a silk thread to a wire connected to a force transducer on one end and fixed with silk ties to a metallic support on the other end. The organ chambers contained physiologic salt solution composed of $NaCl_2$, 118.3 mM; KCl, 4.7 mM; $MgSO_4$, 0.6 mM; $KH_2PO_4$, 1.2 mM; $CaCl_2$, 2.5 mM; $NaHCO_3$, 25 mM: calcium EDTA, 0.026 mM and glucose 11.1 mM/. The solution was gassed with 95% oxygen and 5% carbon dioxide. The temperature was maintained at 37° C. To obtain optimal resting isometric tension for contraction, the strips were stepwise stretched for a period of approximately two hours. Resting tension was adjusted to the optimal isometric tension for contraction for each group by determining the tension at which contraction to phenylephrine ($1 \times 10^{-6}$ M) was maximal. After the initial equilibration in the organ bath, the tissues were optimally stretched and contracted with phenylephrine. Once a steady contraction was obtained, the tissues were relaxed by the addition of the phosphodiesterase inhibitors, Sildenafil and Dipyridamol or l-deprenyl. In some studies the phosphodiesterase inhibitors were added prior to contraction with phenylephrine and then l-deprenyl was added. The results were expressed as percent of phenylephrine induced contraction.

3. Measurement of cGMP

The penile segments in triplicate was placed in 200 µl of DMEM buffer at 37° C. and gassed with 95% air and 5% carbon dioxide and equilibrated for an hour with occasional removal of the buffer (3-4 times) and replacement with fresh buffer. The various drugs were added to the buffer and the incubations were continued for another 10 min. The reactions were stopped by the addition of 200 µL of 1 mol/L perchloric acid and the tissues were sonicated for 60 sec. After centrifugation at 1000×g for 15 minutes, the supernatants were removed and neutralized with 1 mol/L $K_3PO_4$. Aliquots were taken and then acetylated with triethylamine/acetic anhydride (1:2, v/v). After appropriate dilution with phosphate buffer, the cGMP concentrations were measured by radioimmunoassay.

What is claimed is:

1. A method for treating erectile dysfunction in a human male, comprising administering to the human male in need thereof an effective amount of a pharmaceutical composition comprising:

a phosphodiesterase type 5 inhibitor and an MAO inhibitor, wherein the MAO inhibitor is a deprenyl or propargylamine compound.

2. A method of claim 1, wherein said phosphodiesterase type 5 inhibitor is selected from the group consisting of sildenafil, tadalafil, vardenafil, avanafil, zaprinast, dipyridamole, 3-isobutyl-1-methylxanthine (IBMX), propentofylline, papaverine, 4-bromo-5-(pryidylmethylamino)-6-[3-(4-chlorophenyl)propxy]-3(2H)pyridazinone, 1-[4-[(1,3-benzodiozol-5-9pyridylmethylamino)-6-chloro-2-quinazolinyl]-4-piperidine-carboxylic acid, (+)-cis-5,6a,7,9,9,9a-hexahydro-2-[4-(trifloromethyl)-phenylmethyl-5-methyl cyclopent-4,5]imidazo[2.1-b]purin-4(3H)one, furazlocillin, cis-2-hexyl-5-methyl3,4,5,6a,7,8,9,9a-octahydrocyclopent[4,5]imidazo[2,1-b]purin-4-one, 3-acetyl-1-(2-chlorobenzyl)-2-propylindole-6-carboxylate, 4-bromo-5-(3-pyridylmethylamino)-6-(3-(4-chlorophenyl)propoxy)-3(2H) pyridazinone, 1-methyl-5-(5morpholinoacetyl-2-n-propoxyphenyl)-3-n-propyl-1,6-dihydro-7H-pyrazolo(4,3-d)pyrimidin-7-one, 1-[4[(1,3-benzyodioxol-5-methyl) amino]-6-chloro-2-quinazolinyl]4-piperidine carboxylic acid, and salts thereof.

3. A method according to claim 2, wherein the phosphodiesterase type 5 inhibitor is sildenafil.

4. A method according to claim 2, wherein the phosphodiesterase type 5 inhibitor is tadalafil.

5. A method according to claim 2, wherein the phosphodiesterase type 5 inhibitor is vardenafil.

6. A method according to claim 2, wherein the phosphodiesterase type 5 inhibitor is zaprinast.

7. A method according to claim 2, wherein the phosphodiesterase type 5 inhibitor is dipyridamole.

8. A method according to claim 2, wherein the human male is administered daily doses of phosphodiesterase type 5 inhibitor in the range of 0.1 to 500 mg per day.

9. A method according to claim 1, wherein the compound administered with phosphodiesterase type 5 inhibitor is selected from a group of monoamine oxidase type A and B inhibitors consisting of l-deprenyl (selegiline), d-deprenyl, desmethyl selegiline, clorgyline, pargyline, iproniazid, nialamide, phenelzine, tranylcypromine, quinacrine, barboxamide, RO 16-6491, RO 41-1049, Lazabemide, rasagiline, N-propargylamine.

10. A method according to claim 9, wherein the l-deprenyl or proparylamine compounds enhance the biological actions of phosphodiesterase type 5 inhibitors by stimulating the activity of endothelial NOS and neuronal NOS, increasing production of nitric oxide resulting in increased generation of cyclic GMP.

11. A method according to claim 9, wherein the deprenyl or propargylamine compounds enhance the biological actions of phosphodiesterase type 5 inhibitors, facilitate rapid and prolonged clinical effect by vascular, neuronal, antioxidant, anti-atherogenic, anti-platelet, and anti-inflammatory, antidiabetic, antiapoptotic, enhanced dopamine activity, and antidepressant actions.

12. A method according to claim 9, wherein the human male is administered daily doses of monoamine oxidase inhibitor in the range of 0.1 to 500 mg per day.

13. A method according to claim 1, wherein the erectile dysfunction is vasculogenic impotence, caused by vascular disease or diabetes.

14. A method according to claim 1, wherein the erectile dysfunction is psychogenic.

15. A method according to claim 1, wherein the erectile dysfunction is neurogenic.

16. A method according to claim 1, wherein the erectile dysfunction is mixed type.

17. A method according to claim 1, wherein the erectile dysfunction is drug-induced.

18. A method for treating erectile dysfunction in a human male, comprising:
   administering to the human male in need thereof, an effective amount of a pharmaceutical composition comprising a phosphodiesterase type 5 inhibitor; and an MAO inhibitor selected from
   deprenyl or propargylamine compounds, to enhance the effects of other modalities of treatment.

19. A method according to claim 18, wherein the modalities of treatment are selected from a group consisting of psychotherapy, surgical methods, penile implants, vacuum methods.

* * * * *

UNITED STATES PATENT AND TRADEMARK OFFICE
CERTIFICATE OF CORRECTION

PATENT NO. : 7,737,147 B2 Page 1 of 1
APPLICATION NO. : 10/881911
DATED : June 15, 2010
INVENTOR(S) : Thomas Nadackal Thomas It is certified that error appears in the above-identified patent and that said Letters Patent is hereby corrected as shown below:

Title Page, Item (63) Related U.S. Application Data:

Delete "6,635,337" insert --6,635,667--.

Signed and Sealed this

Fifth Day of October, 2010

David J. Kappos
*Director of the United States Patent and Trademark Office*